United States Patent [19]

Aya et al.

[11] 4,132,543
[45] Jan. 2, 1979

[54] PROMOTING SELECTIVE GROWTH OF RICE IN PADDIES

[75] Inventors: Masahiro Aya; Nobuo Fukazawa; Kazuo Kurihara; Itsuro Kobori, all of Tokyo, Japan

[73] Assignee: Bayer Aktiengesellschaft, Leverkusen, Germany

[21] Appl. No.: 493,431

[22] Filed: Jul. 31, 1974

[30] Foreign Application Priority Data

Aug. 8, 1973 [JP] Japan .................................. 48-88521

[51] Int. Cl.$^2$ ............................................. A01N 9/00
[52] U.S. Cl. .......................................... 71/88; 71/67; 71/87; 71/94; 71/98; 71/100
[58] Field of Search ...................... 71/98, 100, 67, 87, 71/120, 88, 94; 424/225

[56] References Cited

U.S. PATENT DOCUMENTS

| | | | |
|---|---|---|---|
| 3,746,532 | 7/1973 | Kimura et al. | 71/100 |
| 3,863,474 | 2/1975 | Kudamatsu et al. | 71/100 |

OTHER PUBLICATIONS

Klauke et al., "Herbicidal N-[(difluorochloromethylthio)aryl]etc.", (1971), CA 75, No. 98343k (1971).
Johnson, "Comb. of Herbicides and Other Pesticides etc.", (1970), CA 72, No. 110464a, (1970).
Inoue et al., "Smaller Brown Planthopper etc.", (1969), CA 75, No. 4510n, (1971).
Farbenfabriken Bayer, "Synergistic Herbicidal, etc.", (1972), CA 78, No. 12692a, (1973).

Primary Examiner—Glennon H. Hollrah
Attorney, Agent, or Firm—Sprung, Felfe, Horn, Lynch & Kramer

[57] ABSTRACT

The selective growth of rice in paddies is promoted by applying thereto a composition comprising
(a) a thiolcarbamate of the formula

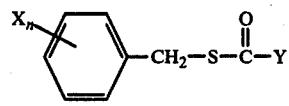

wherein
X is halogen or a lower alkoxy or lower alkyl radical,
Y is a dialkylamino, hexamethylenimino or 2-methylpiperidino radical, and
n is 1 or 2, (if n is 2 the X radicals may be identical or different)
(b) a phenylurea of the formula

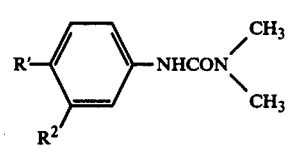

wherein
one of R' and $R^2$ is difluorochloromethylmercapto and the other is difluorochloromethylmercapto, chloro or hydrogen, and
(c) O,O-diethyl-S-(2-ethylmercaptoethyl)-thionothiolphosphate.

16 Claims, No Drawings

PROMOTING SELECTIVE GROWTH OF RICE IN PADDIES

The present invention relates to novel compositions comprising particular substituted-benzylthiolcarbamates, N,N-dimethyl-N'-substituted-phenyl-ureas and O,O-diethyl-S-(2-ethylmercaptoethyl)-thionophosphate, and to the use of such compositions in the cultivation of rice.

In the cultivation of rice in paddies, in an effort to save labor the sowing, cultivation and transplanting of rice seedlings has been mechanized. Transplanting has been hindered, however, by a phenomenon resulting in loss of the transplants. Specifically, algae such as Spirogyra sp. and *Hydrodictyon reticulatum Lagerkeim* grew on the surface of the soil and formed large continuous areas. When the paddy was flooded, the areas of algae floated to the top and the rice seedlings which projected therethrough were so securely held that they were carried out of the soil.

Investigation and researchers revealed that growth of these algae in a manner which resulted in loss of the seedlings could be prevented without damage to the rice and simultaneously with combatting weeds and insect pests which interfered with maximum rice growth and yield.

In accordance with the present invention there is applied to the rice paddy a composition comprising (a) a thiolcarbamate of the formula

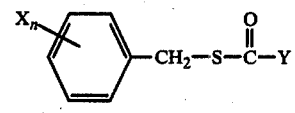

wherein
X is halogen or a lower alkoxy or lower alkyl radical,
Y is a dialkylamino, hexamethylanimino or 2-methylpiperidino radical, and
n is 1 or 2, (if n is 2 the X radicals may be identical or different)
(b) a phenylurea of the formula

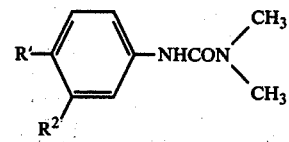

wherein
one of R' and $R^2$ is difluorochloromethylmercapto and the other is difluorochloromethylmercapto, chloro or hydrogen, and
(c) O,O-diethyl-S-(2-ethylmercaptoethyl)-thionothiolphosphate.

Preferably, in ingredient (a) X is 4-chloro-, 2,5-dichloro-, 2-chloro-5-bromo-, 4-methoxy, 4-isopropyl-, 3-chloro-4-isopropoxy-, 2,5-dimethyl- or 3-chloro-4-methoxy. Y is preferably dimethylamino-, diethylamino-, diisopropylamino-, N,N-hexamethylenimino- or N,N-(1-methyl-pentamethylenimino)-.

The individual compounds (a), (b) and (c) are known in the art and preferred individual examples of the compounds and their physical properties are as follows:

TABLE 1

| Compound No. | Structural formula | Physical constant |
|---|---|---|
| I-A | CH₃O—⌬—CH₂—S—C(=O)—N(C₂H₅)₂ | b.p. 162 – 163° C/0.9 – 1 mmHg |
| I-B | Cl—⌬—CH₂—S—C(=O)—N(C₂H₅)₂ | b.p. 142 – 145° C/0.5 mmHg |
| I-C | 2,5-(CH₃)₂—⌬—CH₂—S—C(=O)—N(CH₃)₂ | b.p. 138 – 141° C/0.15 mmHg |
| I-D | iso-C₃H₇O—⌬(Cl)—CH₂—S—C(=O)—N(C₂H₅)₂ | m.p. 37 – 38° C |
| I-E | Cl—⌬—CH₂—S—C(=O)—N(hexamethylenimino) | m.p. 59 – 60° C |

TABLE 1-continued

| Compound No. | Structural formula | Physical constant |
|---|---|---|
| I-F | Cl—⟨phenyl⟩—CH$_2$—S—C(=O)—N(CH$_3$)(cyclohexyl-H) | b.p. 168 – 172° C/0.5 mmHg |

TABLE 2

| Compound No. | Structural formula | Physical constant |
|---|---|---|
| II-A | ClF$_2$C—S—⟨phenyl, Cl⟩—NH—CO—N(CH$_3$)$_2$ | m.p. 112° C |
| II-B | ClF$_2$C—S—⟨phenyl⟩—NH—CO—N(CH$_3$)$_2$ | m.p. 142–145° C |
| II-C | ⟨phenyl, S—CF$_2$Cl⟩—NH—CO—N(CH$_3$)$_2$ | m.p. 114° C |
| II-D | Cl—⟨phenyl, S—CF$_2$Cl⟩—NH—CO—N(CH$_3$)$_2$ | |

TABLE 3

| Compound No. | Structural formula | Physical properties |
|---|---|---|
| III | (C$_2$H$_5$O)$_2$P(=S)—S—CH$_2$—CH$_2$SC$_2$H$_5$ | b.p. 62°C/0.01mmHg $n_D^{20}$ 1.5348 |

The novel composition can be applied at any stage of the rice cultivation during which it is desired to realize the beneficial effect. Weeds which have already sprouted, such as gramineae weeds can be simultaneously controlled. Particularly efficacious results are realized when the material is applied from about one week prior to rice planting up until two weeks after it is completed. The results using the novel mixture are superior to the results using the components individually and are greater than could have been expected.

Advantageously, the ingredients are combined and applied in about 4 to 30 g per are of (a), about 2 to 8 g per are of (b) and about 10 to 35 g per are of (c).

The active materials used according to the present invention can be converted into the usual formulations, such as solutions, emulsions, suspensions, tablets, fumigants, aerosols, powders, pastes and granulates. These may be produced in known manner, for example by mixing the active compounds with extenders, that is, liquid or solid or liquefied gaseous diluents or carriers, optionally with the use of surface-active agents, that is, emulsifying agents and/or dispersing agents. In the case of the use of water as an extender, organic solvents can, for example, also be used as auxiliary solvents.

As liquid diluents or carriers, there are preferably used aromatic hydrocarbons, such as xylenes, toluene, benzene or alkyl naphthalenes, chlorinated aromatic or aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethyl formamide, dimethyl sulphoxide or acetonitrile, as well as water.

By liquefied gaseous diluents or carriers are meant liquids which would be gaseous at normal temperatures and pressures, for example aerosol propellants, such as halogenated hydrocarbons, for example freon.

As solid diluents or carriers, they are preferably used ground natural minerals, such as kaolins, clays, talc, chalk, quartz, attapulgite, montmorillonite or diatomaceous earth, or ground synthetic minerals, such as highly-dispersed silicic acid, alumina or silicates.

Preferred examples of emulsifying agents include non-ionic and anionic emulsifiers, such as polyoxyethylene-fatty acid esters, polyoxyethylene-fatty alcohol ethers, for example alkylarylpolyglycol ethers, alkyl sulphonates, alkyl sulphates and aryl sulphonates; and preferred examples of dispersing agents include lignin, sulphite waste liquors and methyl cellulose.

Possible adjuvants include organic matter, stabilizers, adhesive agents, for example soap, calcium caseinate, sodium alginate, polyvinyl alcohol, steeping agents, coumarone (or indene) resins or polyvinyl butyl ether, combustible materials (for fumigants), for example nitrites, zinc dust or dicyandiamide, oxygen-yielding substances, for example perchlorates or dichromates, phytotoxicity-reducing substances, for example zinc sulphate, ferrous chloride or copper nitrate, substances for prolonging the biological effect, for example chlorinated terphenyls, emulsion-stabilizing substances, for example casein, gum tragacanth and carboxymethyl cellulose (polyvinyl alcohol also being suitable for this purpose), and synergistic agents.

The formulations contain, in general, from 0.1 to 95% preferably from 0.5 to 90%, by weight of the total active compounds.

The materials of the present invention can, if desired, be applied with other agricultural chemicals such as insecticides, acaricides, nematocides, antiviral agents, herbicides, plant-growth regulators and attractants, as well as with fertilizers.

The ready-to-use preparations (which may be prepared from suitable formulations by, for instance, dilution with water) may be applied in any usual manner, for instance, by spraying, such as liquid spraying, misting, atomizing, dusting, scattering, watering, pouring, fumigating, by soil application, such as mixing, sprinkling, vaporising and irrigating, by surface application, such as painting, banding and dressing (dust-coating), or by immersion.

The amount of the total active material in the ready-to-use preparation is generally from 0.0001–20% by weight, preferably 0.005-10% by weight. The quantity of the total active ingredients can be varied according to the type of preparation used, the method, purpose, time and place of the application and the growth state of the weeds to be controlled.

The compounds to be used according to the present invention may be also used in accordance with the well-known ultra-low-volume (ULV) process. According to this method, it is possible to use a concentration of the total active ingredients of up to 95%, or even to apply the active compounds alone.

The dosage per unit area is generally 250 to 700 g, preferably 300 to 600 g, by weight of total active compounds per 10 ares. However, it is possible to increase or reduce the usual amount and, in special cases, it may actually be necessary to do so.

The compositions of the present invention are illustrated in and by the following Examples, in which the active compounds are identified by the numbers assigned to them in Tables 1, 2 and 3.

EXAMPLE (I)

2 parts by weight of compound No. II-A, 8 parts by weight of compound No. I-E, 16 parts by weight of ethylthiometon, 72 parts by weight of a mixture of diatomaceous earth and kaolin (1:5) and 2 parts by weight of an emulsifier, "Runnox" (a polyoxyethylene alkalaryl ether) are mixed and crushed to prepare a wettable powder. This formulation may be diluted with water to the desired concentration and then applied by spraying.

EXAMPLE (II)

2 parts by weight of compound No. II-A, 6 parts by weight of compound NO. I-A, 12 parts by weight of ethylthiometon 45 parts by weight of xylene, 15 parts by weight of "Kawakasol" (aromatic hydrocarbons with a high boiling point) and 20 parts by weight of "Sorpol" (a polyoxyethylene alkylaryl ether) are mixed and stirred to prepare an emulsifiable concentrate. This formulation may be diluted with water to the desired concentration and then applied by spraying.

EXAMPLE (III)

1 part by weight of compound No. II-A, 4 parts by weight of compound No. I-C, 8 parts by weight of ethylthiometon and 87 parts by weight of a mixture of talc and clay (1:3) are mixed and crushed to prepare a dust. This formulation may be applied by dusting.

EXAMPLE (IV)

1 part by weight of compound No. II-A, 4 parts by weight of compound No. I-E and 8 parts by weight of ethylthiometon were solved to 10 parts by weight of dimethylformamide (DMF) and 3 parts by weight of ligninsulfonic acid salt by heating. The solution is adsorbed uniformly by 84 parts by weight of pumice particles with a particle size distribution of 0.5-2mm (8-32 mesh) in order to obtain granules. This formulation may be applied by spraying.

EXAMPLE (V)

3 parts by weight of compound No. I-F, 1 part by weight of compound No. II-A, 6 parts by weight of ethylthiometon, 10 parts by weight of bentonite, 78 parts by weight of a mixture of talc and clay (1:3) and 2 parts by weight of lignin sulphate are mixed. To this mixture 25 parts by weight of water are added, and then the mixture is kneaded and finely devided by means of an extruding granulator to prepare granules of 20-40 mesh, which are dried at 40°-50° C. This formulation may be applied by scattering.

EXAMPLE (VI)

2 parts by weight of compound No. II-A, 8 parts by weight of compound No. I-D were solved in 7 parts by weight of dimethylformamide (DMF), 2 parts by weight of ligninsulfonic acid salt by heating.

The solution is adsorbed uniformly by 81 parts by weight of clay particles with a particle size distribution of 1.5-2 mm (8-32 mesh) to obtain granules. The mixture was intimately blended and finely divided by means of a granulator. This formulation may be applied by scattering.

The invention is further described in the following illustrative examples:

EXAMPLE 1

Test against paddy weeds under irrigation condition with soil treatment and the prevention of seedling loss (pot test)

Preparation of active material
 carrier: 5 parts by weight of acetone or talc
 emulsifier: 1 part by weight of benzyloxypolyglycolether 1 part by weight of active material and the above mentioned amount of the emulsifier and carrier were mixed and formulated into emulsifiable concentrates or wettable powders. The mixture was diluted with water to the desired concentration.

Test procedures

Wagner pots (1/5,000 are) were filled with soil from a rice paddy. Two rice plant seedlings (Kinmaze variety) about 10 cm high at the two-leaved stage were transplanted per pot. Seeds of barnyard grass (*Echinochloa crusgalli*), flat sedges (*Cyperus microiria*), *Monochoria vaginalis* and broad leaved weeds were sown, and spikerushes (*Eleocharis acicularis*) and liquid of *Hydrodictyon reticulatum Lagerheim* were transplanted in the soil.

Thereafter, the pot was kept wet. After 2 days, the pot was irrigated to a depth of 3 cm, and the soil was treated with the emulsion containing the prescribed amount of the active material by means of a pipette. After application, the irrigation water was discharged for 2 days at a rate of 2-3 cm per day, and was thereafter maintained at a depth of about 3 cm. After 3 weeks, the herbicidal effect and the phytotoxicity to the sample rice plant were evaluated and classified on the following scales ranging from 0 to 5. Furthermore, the preventive seedling loss efficacy was evaluated and classified according to the following standard. The test results are average values of two tests.

Evaluation

| Herbicidal Effects | Herbicidal activity in comparison with untreated area |
|---|---|
| 5: | More than 95% of weeds killed |
| 4: | More than 80% |
| 3: | More than 50% |
| 2: | More than 30% |
| 1: | More than 10% |
| 0: | Less than 10% (no significant) |

| Phytotoxicity | Phytotoxic activity in comparison with untreated area |
|---|---|
| 5: | More than 90% of rice plants killed |
| 4: | More than 50% |

-continued

3: More than 30%
2: Less than 30%
1: Less than 10%
0: (no phytotoxicity)

The efficacy in prevention of seedling loss is expressed according to the following standard:
+++: loss occurred over more than 50% of the pot area
++: loss occurred over more than 20% of the pot area
+: loss occurred over less than 20% of the pot area
—: no occurrence

TABLE 4

Test results against paddy weeds under irrigation conditions with soil treatment and the test results of the prevention of seedling loss (pot test)

| Composition | Active material g/10 are | | | Herbicidal Effects | | | | | | Efficacy in preventing seedling loss | Phytotoxicity to rice plants |
|---|---|---|---|---|---|---|---|---|---|---|---|
| | I | II | III | Barnyard grass | Spike-rush | Flat sedge | Monochoria vaginalis | Broad-leaved weeds | Hydrodictyon reticulatum Lagerheim | | |
| I-A | 50 | 0 | 0 | 3 | 0 | 2 | 0 | 0 | 0 | +++ | 0 |
| | 100 | 0 | 0 | 4.5 | 2 | 3 | 0 | 3 | 0 | +++ | 0 |
| | 150 | 0 | 0 | 5 | 3 | 4 | 2 | 4 | 0 | +++ | 0 |
| I-B | 50 | 0 | 0 | 3.5 | 2 | 2 | 3 | 2 | 0 | +++ | 0 |
| | 100 | 0 | 0 | 4 | 3 | 3 | 3.5 | 3 | 0 | +++ | 0 |
| | 150 | 0 | 0 | 5 | 4 | 4 | 4 | 4 | 0 | +++ | 0 |
| I-C | 50 | 0 | 0 | 2 | 0 | 2 | 0 | 0 | 0 | +++ | 0 |
| | 100 | 0 | 0 | 3 | 2 | 3 | 0 | 3 | 0 | +++ | 0 |
| | 150 | 0 | 0 | 4 | 3 | 4 | 2 | 4 | 0 | +++ | 0 |
| I-D | 50 | 0 | 0 | 2 | 2 | 2 | 0 | 0 | 0 | +++ | 0 |
| | 100 | 0 | 0 | 3 | 3 | 3 | 0 | 3 | 0 | +++ | 0 |
| | 150 | 0 | 0 | 4.5 | 4 | 3–4 | 2 | 4 | 0 | +++ | 0 |
| I-E | 50 | 0 | 0 | 3.5 | 2 | 2 | 3 | 2 | 0 | +++ | 0 |
| | 100 | 0 | 0 | 4.5 | 3 | 3.5 | 4 | 4 | 0 | +++ | 0 |
| | 150 | 0 | 0 | 5 | 4 | 4 | 4 | 4 | 0 | +++ | 0 |
| I-F | 50 | 0 | 0 | 3.4 | 2 | 2 | 3 | 2 | 0 | +++ | 0 |
| | 100 | 0 | 0 | 4 | 3 | 3.5 | 4 | 4 | 0 | +++ | 0 |
| | 150 | 0 | 0 | 5 | 4 | 4 | 4 | 4 | 0 | +++ | 0 |
| II-A | 0 | 25 | 0 | 2 | 2 | 4 | 4 | 4 | 3 | — | 0 |
| | 0 | 50 | 0 | 3.5 | 3 | 5 | 5 | 5 | 4 | — | 0 |
| | 0 | 75 | 0 | 4.5 | 4 | 5 | 5 | 5 | 5 | — | 0 |
| | 0 | 100 | 0 | 5 | 5 | 5 | 5 | 5 | 5 | — | 0 |
| III | 0 | 0 | 100 | 0 | 0 | 0 | 0 | 0 | 0 | ++ | 0 |
| | 0 | 0 | 200 | 0 | 0 | 0 | 0 | 0 | 0 | ++ | 0 |
| | 0 | 0 | 300 | 0 | 0 | 0 | 0 | 0 | 0 | ++ | 0 |
| I-A + II-A | 100 | 25 | 0 | 5 | 5 | 5 | 5 | 5 | 4 | + | 0 |
| | 150 | 50 | 0 | 5 | 5 | 5 | 5 | 5 | 5 | + | 0 |
| I-B + II-A | 100 | 25 | 0 | 5 | 5 | 5 | 5 | 5 | 4.5 | + | 0 |
| | 150 | 50 | 0 | 5 | 5 | 5 | 5 | 5 | 5 | + | 0 |
| I-C + II-A | 100 | 25 | 0 | 5 | 5 | 5 | 5 | 5 | 4 | + | 0 |
| | 150 | 50 | 0 | 5 | 5 | 5 | 5 | 5 | 5 | + | 0 |
| I-D + II-A | 100 | 25 | 0 | 5 | 5 | 5 | 5 | 5 | 4 | + | 0 |
| | 150 | 50 | 0 | 5 | 5 | 5 | 5 | 5 | 5 | + | 0 |
| I-E + II-A | 100 | 25 | 0 | 5 | 5 | 5 | 5 | 5 | 4 | + | 0 |
| | 150 | 50 | 0 | 5 | 5 | 5 | 5 | 5 | 5 | + | 0 |
| I-F + II-A | 100 | 25 | 0 | 5 | 5 | 5 | 5 | 5 | 4.5 | + | 0 |
| | 150 | 50 | 0 | 5 | 5 | 5 | 5 | 5 | 5 | + | 0 |
| I-A + III | 100 | 0 | 200 | 4.5 | 3 | 4 | 0 | 4 | 0 | +++ | 0 |
| | 150 | 0 | 300 | 5 | 4 | 4 | 3 | 4 | 0 | +++ | 0 |
| I-B + III | 100 | 0 | 200 | 4 | 3 | 3 | 4 | 3 | 0 | +++ | 0 |
| | 150 | 0 | 300 | 5 | 4 | 4 | 4.5 | 4 | 0 | +++ | 0 |
| I-C + III | 100 | 0 | 200 | 4.5 | 3.5 | 3 | 2 | 3 | 0 | +++ | 0 |
| | 150 | 0 | 300 | 5 | 4 | 4 | 3 | 4 | 0 | +++ | 0 |
| I-D + III | 100 | 0 | 200 | 4.5 | 3 | 3 | 2 | 3 | 0 | +++ | 0 |
| | 150 | 0 | 300 | 5 | 4 | 4 | 3 | 4 | 0 | +++ | 0 |
| I-E + III | 100 | 0 | 200 | 4 | 3 | 4 | 4 | 4 | 0 | +++ | 0 |
| | 150 | 0 | 300 | 5 | 4 | 4 | 4 | 5 | 0 | +++ | 0 |
| I-F + III | 100 | 0 | 200 | 4 | 3 | 4 | 4 | 4 | 0 | +++ | 0 |
| | 150 | 0 | 300 | 5 | 4 | 4 | 4 | 4 | 0 | +++ | 0 |
| II + III | 0 | 25 | 100 | 3 | 2 | 4.5 | 5 | 5 | 3.5 | — | 0 |
| | 0 | 50 | 200 | 4 | 3 | 5 | 5 | 5 | 4 | — | 0 |
| | 0 | 75 | 300 | 5 | 4 | 5 | 5 | 5 | 5 | — | 0 |
| I-A + *II-A + III | 100 | 25 | 200 | 5 | 5 | 5 | 5 | 5 | 4.5 | — | 0 |
| | 150 | 50 | 300 | 5 | 5 | 5 | 5 | 5 | 5 | — | 0 |
| I-B + *II-A + III | 100 | 25 | 200 | 5 | 5 | 5 | 5 | 5 | 4.5 | — | 0 |
| | 150 | 50 | 300 | 5 | 5 | 5 | 5 | 5 | 5 | — | 0 |
| I-C + *II-A | 100 | 25 | 200 | 5 | 5 | 5 | 5 | 5 | 4.5 | — | 0 |

TABLE 4-continued

Test results against paddy weeds under irrigation conditions with soil treatment and the test results of the prevention of seedling loss (pot test)

| Composition | Active material g/10 are I | II | III | Barnyard grass | Spike-rush | Flat sedge | Monochoria vaginalis | Broad-leaved weeds | Hydrodictyon reticulatum Lagerheim | Efficacy in preventing seedling loss | Phytotoxicity to rice plants |
|---|---|---|---|---|---|---|---|---|---|---|---|
| + III | 150 | 50 | 300 | 5 | 5 | 5 | 5 | 5 | 5 | — | 0 |
| I-D + *II-A | 100 | 25 | 200 | 5 | 5 | 5 | 5 | 5 | 4.5 | — | 0 |
| + III | 150 | 50 | 300 | 5 | 5 | 5 | 5 | 5 | 5 | — | 0 |
| I-E + *II-A | 100 | 25 | 200 | 5 | 5 | 5 | 5 | 5 | 4.5 | — | 0 |
| + III | 150 | 50 | 300 | 5 | 5 | 5 | 5 | 5 | 5 | — | 0 |
| I-F + *II-A | 100 | 25 | 200 | 5 | 5 | 5 | 5 | 5 | 4.5 | — | 0 |
| + III | 150 | 50 | 300 | 5 | 5 | 5 | 5 | 5 | 5 | — | 0 |
| Untreated | — | — | — | 0 | 0 | 0 | 0 | 0 | 0 | ++ | 0 |

Note:
1) I represents the compounds of Table 1.
2) II represents the compounds of Table 2.
3) III represents the compound of Table 3.
4) Broad-leaved weeds: Rotala indica, Lindernia pyxidaria, etc.
5) *mixed formulation in accordance with the invention.

EXAMPLE 2

Test against paddy weeds under irrigation conditions with soil treatment and the prevention of seedling loss (concrete container test)

Test procedure

A concrete container 50 cm long, 50 cm wide and 30 cm high was used. Gravel was placed in the lowermost 3 cm of the container and a layer of sand 3 cm deep was placed thereon. On the sand layer there was placed a 5 cm layer of paddy-field soil, and the layers were then compressed. Screened paddy-field soil was placed thereon in a layer 10 cm deep and paddy-field soil containing seeds of barnyard grass, flat sedges, *Monochoria vaginalis* and broad-leaved weeds was spread thereover in a layer 3 cm deep. Spikerushes and liquid of *Hydrodictyon reticulatum Lagerheim* were transplanted in the soil. At each of four points, two rice plant seedlings (Kinmaze variety) at the two-leaved stage were transplanted. From 3 to 5 days after the transplantation there was applied the indicated amounts of the active materials in the form of an emulsion or wettable powder, prepared in the manner described in Example 1. Immediately after treatment, the irrigation water was discharged for 2 days at a rate of 3 cm per day, and then maintained at a depth of 4 cm. Three days after treatment, 10 paddy-field rice seeds were sown. Thirty days after treatment, the herbicidal effects and the phytotoxicity against rice plants were evaluated on the scales described in Example 1. The test results are shown in Table 5. The values shown in the table are average values of two tests.

TABLE 5

Test results against paddy-field weeds under irrigation conditions with soil treatment and the test results of the prevention of seedling loss (concrete container test)

| Composition | Active material g/10 are I | II | III | Barnyard grass | Spikerush | Flat sedge | Monochoria vaginalis | Broad-leaved weeds | Efficacy in preventing seedling loss | Phytotoxicity transplanted Rice | directly sown Rice |
|---|---|---|---|---|---|---|---|---|---|---|---|
| I-A | 140 | 0 | 0 | 2 | 2 | 3 | 0 | 0 | +++ | 0 | 0 |
|  | 210 | 0 | 0 | 4 | 3 | 4 | 0 | 0 | +++ | 0 | 0 |
| I-B | 140 | 0 | 0 | 3 | 3 | 3 | 2 | 3 | +++ | 0 | 2 |
|  | 210 | 0 | 0 | 4 | 3.5 | 4 | 3 | 4 | +++ | 0 | 3 |
| I-C | 140 | 0 | 0 | 2 | 2 | 2 | 0 | 0 | +++ | 0 | 0 |
|  | 210 | 0 | 0 | 4 | 3 | 3 | 0 | 0 | +++ | 0 | 0 |
| I-D | 140 | 0 | 0 | 2 | 2 | 2 | 0 | 2 | +++ | 0 | 2 |
|  | 210 | 0 | 0 | 4 | 3 | 3 | 0 | 3 | +++ | 0 | 3 |
| I-E | 140 | 0 | 0 | 3 | 3 | 3 | 3 | 3 | +++ | 0 | 2 |
|  | 210 | 0 | 0 | 4 | 3 | 4 | 4 | 4 | +++ | 0 | 3 |
| I-F | 140 | 0 | 0 | 3 | 3 | 3 | 3 | 3 | +++ | 0 | 2 |
|  | 210 | 0 | 0 | 4 | 4 | 4 | 4 | 4 | +++ | 0 | 3 |
| II-A | 0 | 50 | 0 | 1 | 3 | 4.5 | 5 | 5 | — | 0 | 1 |
|  | 0 | 75 | 0 | 2 | 3 | 5 | 5 | 5 | — | 0 | 2.5 |
| III | 0 | 0 | 300 | 0 | 0 | 0 | 0 | 0 | ++ | 0 | 0 |
| I-A + II-A | 140 | 50 | 0 | 4.5 | 4 | 5 | 5 | 5 | + | 0 | 1 |
|  | 210 | 75 | 0 | 5 | 5 | 5 | 5 | 5 | + | 0 | 2 |
| I-B + II-A | 140 | 50 | 0 | 4.5 | 4 | 5 | 5 | 4 | + | 0 | 1 |
|  | 210 | 75 | 0 | 5 | 5 | 5 | 5 | 5 | + | 0 | 2 |
| I-C + II-A | 140 | 50 | 0 | 4.5 | 4 | 5 | 5 | 5 | + | 0 | 1 |
|  | 210 | 75 | 0 | 5 | 5 | 5 | 5 | 5 | + | 0 | 2 |
| I-D + II-A | 140 | 50 | 0 | 4.5 | 4 | 5 | 5 | 4 | + | 0 | 1 |
|  | 210 | 75 | 0 | 5 | 5 | 5 | 5 | 5 | + | 0 | 2 |
| I-E + | 140 | 50 | 0 | 4.5 | 4 | 5 | 5 | 5 | + | 0 | 1 |

TABLE 5-continued

Test results against paddy-field weeds under irrigation conditions
with soil treatment and the test results of the prevention of seedling
loss (concrete container test)

| Composition | Active material g/10 are | | | Herbicidal Effects | | | | | Efficacy in preventing seedling loss | Phytotoxicity | |
| | I | II | III | Barnyard grass | Spikerush | Flat sedge | Monochoria vaginalis | Broad-leaved weeds | | trans-planted Rice | directly sown Rice |
|---|---|---|---|---|---|---|---|---|---|---|---|
| II-A | 210 | 75 | 0 | 5 | 5 | 5 | 5 | 5 | + | 0 | 2 |
| I-F + | 140 | 50 | 0 | 4.5 | 4 | 5 | 5 | 5 | + | 0 | 1 |
| II-A | 210 | 75 | 0 | 5 | 5 | 5 | 5 | 5 | + | 0 | 2 |
| I-A *+ | 140 | 50 | 200 | 5 | 4 | 5 | 5 | 5 | + | 0 | 0 |
| II-A + III | 210 | 75 | 300 | 5 | 5 | 5 | 5 | 5 | — | 0 | 1 |
| I-B + *II-A | 140 | 50 | 200 | 5 | 4 | 5 | 5 | 5 | — | 0 | 0 |
| + III | 210 | 75 | 300 | 5 | 5 | 5 | 5 | 5 | — | 0 | 1 |
| I-C + *II-A | 140 | 50 | 200 | 5 | 4 | 5 | 5 | 5 | — | 0 | 0 |
| + III | 210 | 75 | 300 | 5 | 5 | 5 | 5 | 5 | — | 0 | 1 |
| I-D + *II-A | 140 | 50 | 200 | 5 | 4 | 5 | 5 | 5 | — | 0 | 0 |
| + III | 210 | 75 | 300 | 5 | 5 | 5 | 5 | 5 | — | 0 | 1 |
| I-E + *II-A | 140 | 50 | 200 | 4.5 | 4 | 5 | 5 | 5 | — | 0 | 0 |
| + III | 210 | 75 | 300 | 5 | 5 | 5 | 5 | 5 | — | 0 | 1 |
| I-F + *II-A | 140 | 50 | 200 | 4.5 | 4 | 5 | 5 | 5 | — | 0 | 0 |
| + III | 210 | 75 | 300 | 5 | 5 | 5 | 5 | 5 | — | 0 | 1 |
| un-treated | — | — | — | 0 | 0 | 0 | 0 | 0 | ++ | 0 | 0 |

Note:
1) I represents the compounds of Table 1.
2) II represents the compounds of Table 2.
3) III represents the compound of Table 3.
4) Broad-leaved weeds: Rotala indica, Lindernia pyxidaria, etc.
5) *mixed formulation in accordance with the invention.

It will be understood that the specification and examples are illustrative but not limitative of the present invention and that other embodiments within the spirit and scope of the invention will suggest themselves to those skilled in the art.

What is claimed is:

1. A composition promoting the growth of rice consisting essentially of, by weight,
(a) about 4 to 30 parts of a thiolcarbamate of the formula

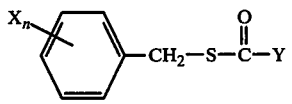

wherein
X is halogen or a lower alkoxy or lower alkyl radical,
Y is a dialkylamino with up to 4 carbon atoms per alkyl radical, hexamethylenimino or 2-methyl-piperidino radical, and
n is 1 or 2, (if n is 2 the X radicals may be identical or different)
(b) about 2 to 8 parts of a phenylurea of the formula

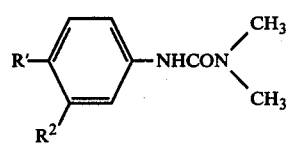

wherein
one of R' and $R^2$ is difluorochloromethylmercapto and the other is difluorochloromethylmercapto, chloro or hydrogen, and
(c) about 10 to 35 parts of O,O-diethyl-S-(2-ethylmercaptoethyl)-thionothiolphosphate.

2. The composition of claim 1 wherein (a) is N,N-diethyl-4-methoxybenzylthiolcarbamate of the formula

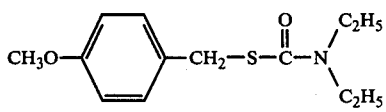

3. The composition of claim 1 wherein (a) is N,N-diethyl-4-chlorobenzylthiolcarbamate of the formula

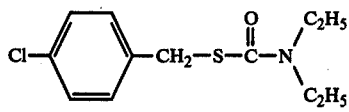

4. The composition of claim 1 wherein (a) is N,N-dimethyl-2,5-dimethylbenzylthiolcarbamate of the formula

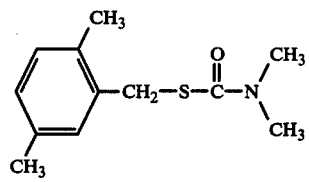

5. The composition of claim 1 wherein (a) is N,N-diethyl-3-chloro-4-isopropoxybenzylthiolcarbamate of the formula

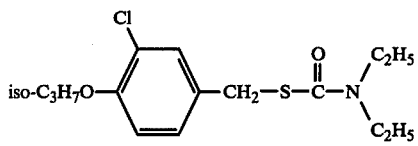

6. The composition of claim 1 wherein (a) is N,N-hexamethylenimino-4-chlorobenzylthiolcarbamate of the formula

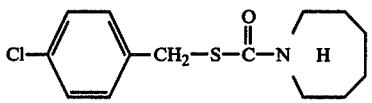

7. The composition of claim 1 wherein (a) is N,N-(1-methylpentamethylenimino)-4-chlorobenzylthiolcarbamate of the formula

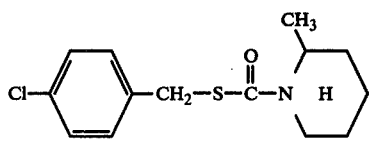

8. The composition of claim 1 wherein (b) is N,N-dimethyl-N'-(3-chloro-4-difluorochloromethylmercapto-phenyl)-urea of the formula

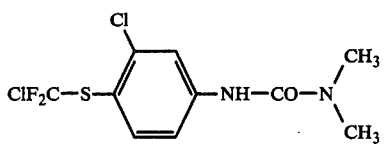

9. The composition of claim 1 wherein (b) is N,N-dimethyl-N'-(4-difluoromethylmercapto-phenyl)-urea of the formula

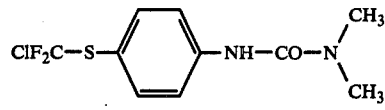

10. The composition of claim 1 wherein (b) is N,N-dimethyl-N'-(3-difluorochloromethylmercapto-phenyl)-urea of the formula

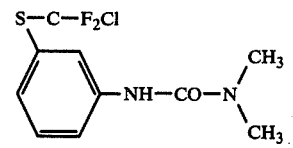

11. The composition of claim 1 wherein (b) is N,N-dimethyl-N'-(3-difluorochloromethylmercapto-4-chloro-phenyl)-urea of the formula

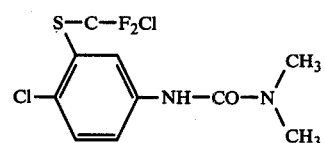

12. The composition of claim 1 wherein
 (a) is a thiolcarbamate wherein Y in the formula is dialkylamino and
 (b) is a phenylurea where one of $R^1$ and $R^2$ is difluorochloromercapto and the other is chloro.

13. The composition of claim 1 wherein X is chlorine, bromine, or alkyl or alkoxy of up to 4 carbon atoms, Y is dialkylamino, and the components (a), (b) and (c) are present in the approximate ratio by weight of 2.8–4:1-:4–8.

14. The method of promoting the growth of rice which comprises applying to a paddy in which rice is grown an effective amount of a composition according to claim 1.

15. The method of claim 14, wherein
 (a) is a member selected from the group consisting of
  N,N-diethyl-4-methoxybenzylthiolcarbamate,
  N,N,diethyl-4-chlorobenzylthiolcarbamate,
  N,N-dimethyl-2,5-dimethylbenzylthiolcarbamate,
  N,N-diethyl-3-chloro-4-isopropoxybenzylthiolcarbamate,
  N-hexamethylimino-4-chlorobenzylthiolcarbamate, and
  N-(1-methyl-pentamethylenimino)-4-chlorobenzylthiolcarbamate, and
 (b) is selected from the group consisting of
  N,N-dimethyl-N'-(3-chloro-4-difluorochloromethylmercapto-phenyl)-urea,
  N,N-dimethyl-N'-(4-difluorochloromethylmercaptophenyl)-urea,
  N,N-dimethyl-N'-(3-difluorochloromethylmercaptophenyl)-urea, and
  N,N-dimethyl-N'-(3-difluorochloromethylmercapto-4-chloro-phenyl)-urea.

16. The method of claim 14 wherein the composition is applied prior to flooding of the paddy.

* * * * *